United States Patent
Daskal et al.

(10) Patent No.: US 7,922,676 B2
(45) Date of Patent: Apr. 12, 2011

(54) DISPOSABLE ELECTRIC BANDAGE

(75) Inventors: Shalom Daskal, Ramat Efal (IL); Dov Tamarkin, Maccabim (IL); Zvi Nitzan, Zofit (IL); Nurit Harel, Tel Aviv (IL); Daniela Mavor, Tel Aviv (IL); Giora Arbel, Tel Mond (IL); Shalom Luski, Rehovot (IL); Noam Emanuel, Jerusalem (IL); Dalia Jayes, Modiin (IL)

(73) Assignee: Power Paper, Ltd., Beit Shemesh (IL)

( * ) Notice: Subject to any disclaimer, the term of this patent is extended or adjusted under 35 U.S.C. 154(b) by 1980 days.

(21) Appl. No.: 10/936,540

(22) Filed: Sep. 9, 2004

(65) Prior Publication Data

US 2005/0085751 A1 Apr. 21, 2005

Related U.S. Application Data

(60) Provisional application No. 60/501,402, filed on Sep. 10, 2003.

(51) Int. Cl.
*A61F 5/00* (2006.01)
(52) U.S. Cl. .................. 602/2; 602/41; 602/42
(58) Field of Classification Search ........... 602/2, 41–56
See application file for complete search history.

(56) References Cited

U.S. PATENT DOCUMENTS

| | | | |
|---|---|---|---|
| 5,143,089 A * | 9/1992 | Alt ................................ 607/121 |
| 5,811,204 A | 9/1998 | Nitzan et al. |
| 5,935,598 A * | 8/1999 | Sage et al. .................... 424/449 |
| 5,961,483 A * | 10/1999 | Sage et al. ....................... 604/20 |
| 5,974,344 A | 10/1999 | Shoemaker, II et al. |
| 6,185,453 B1 * | 2/2001 | Hussain et al. .................. 604/21 |
| 6,246,904 B1 | 6/2001 | Murdock |
| 6,560,483 B1 | 5/2003 | Kumar et al. |
| 2003/0147835 A1 | 8/2003 | Munro et al. |

FOREIGN PATENT DOCUMENTS

WO   WO 03/035166 A2   5/2003

* cited by examiner

*Primary Examiner* — Michael A. Brown
(74) *Attorney, Agent, or Firm* — Kenyon & Kenyon LLP

(57) ABSTRACT

The present invention provides a device and kit and method of use thereof for wound treatment of a subject. The device may include an electrically operated patch or other means of delivery of electrical current and a connected moist surface. Optionally, the device may include a composition comprising an active substance useful in wound treatment. Preferably, the means of delivery of electrical current includes a power source and a plurality of electrodes disposed in a suitable conformation on a base substrate layer, which readily facilitates electrical contact with the body area of the subject. Preferably, the kit may include a means of delivery of electrical current and a moist surface provided as separate components.

The present invention further provides a thin and flexible device for galvanic treatment to treat wounds with electrical stimulation. Preferably, the device is made using a printing technique.

34 Claims, 7 Drawing Sheets

DISPOSABLE ELECTRIC BANDAGE

This application claims priority to U.S. Provisional Application Ser. No. 60/501,402, filed Sep. 10, 2003 entitled "Disposable Electric Bandage" the content of which is incorporated herein by reference in its entirety.

FIELD OF THE INVENTION

The present invention relates in general to a kit and device for wound treatment and in particular to a kit and device for wound treatment, which combines moist treatment and electrical stimulation and galvanic treatment and a method of use thereof.

BACKGROUND OF THE INVENTION

Open wounds are occasionally difficult to treat. Even in mild cases, optimal care is desirable. It has long been misunderstood that the best way to handle a wound was to allow it to dry out and encourage a scab to form. In the last 40 years research has emerged to contradict this line of thinking. In fact, it is presently known that there are many advantages to keeping wounds moist and covered during the healing process, due to the following properties: Since the natural environment for a living cell requires water, it follows that cells require water to live. Dry cells, like the outer epidermis are usually dead cells. Therefore when a wound is present, the break in the skin surface may allow moisture to escape, resulting in dehydration necrosis (or death) of the superficial cells. This necrosis contributes to the formation of the scab, which also provides very little barrier to continued moisture loss. When moist substance is applied to the wound site it helps to control the loss of moisture to prevent further dehydration necrosis and tissue loss. With this moist environment, the cells at the surface are more likely to survive, than if they were in a dry environment.

Moist surface also provides a cooling sensation resulting in the reduction of pain at the wound site. Further, the moist surface absorbs fluid and exudate at the wound site. In addition, the moist surface covers the wound and protects it from extraneous materials and microorganisms.

The moist surface also provides a cushioning layer that protects the wound area from surface pressure. The moist surface remains in contact with the wound area without sticking to it. This provides for removal that will not disrupt the outer layer of the wound. The moist surface rehydrates the wound bed and softens necrotic tissue.

Scientific studies show that moist wound healing, reduces scar formation thereby reducing discomfort and scarring. Treatment with moist surface is useful in superficial injuries, such as cuts, abrasions, blisters, lacerations, superficial burns, pressure sores, road rash, carpet burns, scrapes, sun burns, friction burns, pressure ulcers, stasis ulcers, diabetic ulcers, foot ulcers, post-surgical wounds.

Moist surfaces can be provided in many ways, such as for example by a hydrogel. Hydrogels may have different characteristics, such as water content, gelling agents, electrolyte content, buffering capacity and pH, which can be controlled in order to attain favorable wound care capabilities.

Galvanic treatment has been known for many years, as a means to deliver drugs and cosmetic active agents into the skin for therapeutic purposes. It is based on known mechanisms, including: (a) iontophoresis, in which a charged ion is repelled from an electrode of the same charge; and (b) electroosmosis, based on the convective movement of solvent that occurs through a charged "pore" in response to the preferential passage of counter-ions when the electric field is applied.

Review of the literature reveals that galvanic treatment is also valuable in the treatment of wounds and scars, via several modes of action, including: accelerated cell regeneration; tissue repair; accelerated cutaneous barrier recovery (even with very low current); improved blood circulation; improved respiration; and scar reduction.

Despite these notions, galvanic treatment has not been widely used in wound therapy, especially because current galvanic treatments comprise stationary, costly power sources, which are not convenient for home use. Moreover, there has not been any notion in the literature, nor in common practice of combining moist wound care and galvanic treatment in wound therapy.

There is thus a recognized need for, and it would be highly advantageous to have an improved method of wound treatment such as use of a galvanic treatment device and kit. Moreover, it would be desirable to have a treatment kit, device and method of use thereof, which incorporates a combination of galvanic treatment and moist surface treatment for treating wounds. It would be advantageous to have such a system, which is thin and flexible and facile to use and has low cost. Preferably, such a system and device should be disposable.

SUMMARY OF THE INVENTION

Embodiments of the present invention include a wound treatment device. Preferably, wound treatment device is a galvanic stimulation device. Preferably, the galvanic stimulation device includes at least one electrically operated device. Most preferably wound treatment device includes at least one active electrode, at least one counter electrode, and a power supply disposed on a base layer. Preferably, the device is thin and flexible. Preferably, the device is made using a printing technique.

Embodiments of the present invention also include a wound treatment kit, wherein the kit is a galvanic stimulation device in combination with a moist treatment system. Preferably, wound treatment kit includes at least one electrically operated device and a moist treatment system. Most preferably, wound treatment kit includes at least one active electrode, at least one counter electrode, a power supply, and a moist treatment surface, such as a hydrogel disposed on a base layer. Preferably, the electrically operated device is thin and flexible.

Embodiments of the present invention also provide a wound treatment device, wherein the device includes a galvanic stimulation device connected to or integrally formed with a moist treatment system.

Embodiments of the present invention also include a wound treatment kit, wherein the kit includes a galvanic stimulation device in combination with a moist treatment system and an agent active, wherein the active agent is effective in treating wounds. Preferably, wound treatment kit includes at least one electrically operated device and a moist treatment system and an active agent effective in treating wounds. Most preferably, wound treatment kit includes at least one active electrode, at least one counter electrode, a power supply, a hydrogel (moist treatment surface) and an active agent, wherein the active agent is effective in treating wounds and wherein the electrically operated device components are disposed on a base layer.

Embodiments of the present invention also include a wound treatment device, wherein the device includes a galvanic stimulation device connected to or integrally formed with an active agent effective in the treatment of wounds.

Embodiments of the present invention also include a wound treatment device, wherein the device includes a galvanic stimulation device connected to or integrally formed with an active agent effective in the treatment of wounds and a moist surface.

Embodiments of the present invention also provide methods of using a wound treatment device and kit for treating a wound.

BRIEF DESCRIPTION OF DRAWINGS

With reference now to the drawings in detail, it is stressed that the particulars shown, are by way of example and for the purposes of illustrative discussion of the preferred embodiment of the present invention only, and are presented for providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the drawings.

DETAILED DESCRIPTION OF THE INVENTION

Figure 1:
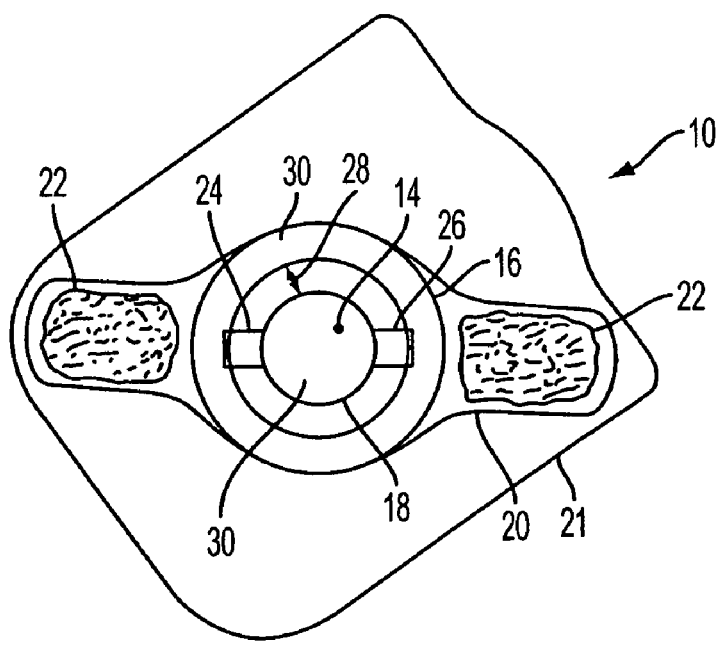
FIG. 1 illustrates a schematic representation of a wound treatment device according to one embodiment of the invention.

Embodiments of the present invention provide a kit for wound treatment of a subject. The kit may include a means of delivery of electrical current and a moist surface. Preferably, the means of delivery of electrical current includes a power source and a plurality of electrodes disposed in a suitable conformation on a base substrate layer, which readily facilitates electrical contact with the body area of the subject.

Embodiments of the present invention also provide a device for wound treatment of a subject. The device includes a means of delivery of electrical current and a moist surface attached to or integrally formed with the means for delivery of electrical current. Optionally, the device can be formed with or include a pharmaceutical composition for treatment of wounds.

Embodiments of the present invention further provide a device for electrical stimulation to treat wounds. The device includes a means for delivery of electric current. Electrical stimulation can readily facilitate reducing congestion in and around wound tissues. Preferably, the device will increase circulation, generating motor and sensory stimulation and peripheral nerve stimulation. Optionally, the device for electrical stimulation can employ direct current, alternating current or pulsed electrical current.

Embodiments of the present invention still further provide a kit for wound treatment, wherein the kit includes an electrically operated device for electrical stimulation, and a composition comprising a pharmaceutical agent also useful in the treatment of superficial injury. Preferably, the kit can also include a moist surface.

Embodiments of the present invention also provide methods of use of the device and kit with or without a pharmaceutical composition for wound treatment.

Embodiments of the present invention advantageously facilitate topically treating superficial injuries, such as, but not limited to cuts, abrasions, blisters, lacerations, superficial burns, pressure sores, road rash, carpet burns, scrapes, sun burns, friction burns, pressure ulcers, stasis ulcers, diabetic ulcers, foot ulcers, post-surgical wounds or combinations thereof.

In one preferred embodiment, devices described herein are useful for wound treating and the like in non-clinical settings, such as the home. Furthermore, in one preferred embodiment, devices described herein utilize one preset voltage and/or current and as such, a user (e.g., the patient) need not adjust the voltage or current of the device.

The term "wound" as used herein refers to any type of wound, including but not limited to superficial injuries, such as, but not limited to cuts, abrasions, blisters, lacerations, superficial burns, pressure sores, road rash, carpet burns, scrapes, sun burns, friction burns, pressure ulcers, stasis ulcers, diabetic ulcers, foot ulcers, scarring, post-surgical wounds, trauma wounds, or combinations thereof.

The terms "treatment" and "therapy" as interchangeably used herein includes any treatment of a superficial injury/wound, and includes: (i) preventing the disease or condition from occurring in a subject which may be predisposed to the disease but has not yet been diagnosed as having it; (ii) inhibiting the disease or condition, i.e. arresting its development; (iii) healing the disease or condition; and (iv) relieving the disease or condition, i.e., causing regression of the disease. In the context of the present invention, relieving the disease, means attaining improvement in the subject condition of an injury, including, but not limited to clinical improvement, microbiological improvement and aesthetic improvement.

Treatment length of time may vary according to the nature and severity of the condition, from a few seconds (such as 10 seconds) to several days.

The terms "device," "iontophoretic device," "iontophoretic patch," "galvanic device", "electrically operated device," "patch" and "electrically operated patch," as used herein, will interchangeably stand for any method or device used for electrical/galvanic stimulation and/or electrical delivery of substances for the treatment of a superficial injury, as described herein, including electrotransportation, iontophoresis, electroosmosis, electroporation, transcutaneous nerve stimulation (TENS), interferential current (IFC) and/or a combination thereof. In a preferred embodiment, the device is a fully or partially printed device, wherein at least one of, or a combination of, or all of, the electrodes, power source, and conductive connections are disposed on a base layer using a suitable printing technique. Preferably, the moist surface and/or active substance is printed onto the device.

FIG. 1 shows one embodiment of a device/patch for treatment of a wound 10 according to the present invention. Preferably, patch 10 is a flexible, wearable patch 10 that can conform and adhere to the skin surface of a person. The patch 10 further includes at least one first electrode 14, identified as "anode", at least one second electrode 16, identified as "cathode" and at least one power source 18, supported on a base member 20 in spaced relation to each other to define a gap therebetween. While the first electrode 14 may be identified as an anode and the second electrode 16 may be identified as a cathode, those of skill will recognize that these designations may be reversed. In the embodiment as illustrated, the base member 20 rests on a release liner 21.

In one preferred embodiment of a round device/patch 10 with concentric arrangement of electrodes 14, 16, inner electrode 14 is preferably the cathode and peripheral electrode is preferably the anode. This arrangement is preferred in a wound healing patch device, such as described in FIG. 1, wherein a large amount of fluids are produced during the healing process. The fluids tend to result in undesirable odor and may interrupt the function of the patch. In such an embodiment, the peripheral anode electrode is preferably the active electrode and is configured for iontophoresis. Preferably, in such an embodiment an absorbing substrate (not shown in FIG. 1), such as a pad is attached to the inner electrode. Preferably, inner electrode is configured to readily remove excess fluids from the wound to be absorbed by the absorbing substrate, by a method such as reverse iontophoresis.

Patch 10 is equipped with a thin power source 18, which, according to certain preferred embodiments, produces direct current (galvanic current), and according to other embodiments, produces an alternating or pulsed electrical current. The choice between direct current and alternating or pulsed current is made according to the nature and severity of the injury and the involvement of pain in the condition.

The device 10 may be of any suitable size and shape, which is effective for use in wound treatment. FIG. 1 shows one non-limiting example of a round device. The width of the device can vary from less than about 1 cm to about 20 cm and the length of the device can range from about 2 cm to about 30 cm. Smaller or larger dimensions are possible. The device 10 is preferably fabricated from thin and flexible materials, which enable at least those surfaces that contact a patients skin to conform to the contours of the patient when the device 10 is applied thereon. Patch 10 may be provided with an adhesive 22 as shown in FIG. 1, that facilitates patch 10 adhering to the wound or surrounding skin/tissue. Alternative attachment means are possible. While illustrated as covering a portion of the base member 20, those of skill in the art will understand that adhesive 22 may cover more or less surface than shown without departing from the scope of the invention.

Preferably, power source 18 has a plurality of terminals, such as a first terminal 24 and a second terminal 26, which may be used to connect the power source to electrodes. As illustrated, both terminals 24, 26 are connected to the same peripheral electrode 16. A third terminal (not shown due to obscuration by the power source) connects the power source 18 to the central electrode 14. This conformation may preferably provide for better current distribution.

As noted, the power source 18 may be connected to two electrodes 14, 16. In an optional embodiment, the power source 18 may be coupled to one of the electrodes of patch 10 or alternatively the power source 18 may be disposed near to electrodes 14, 16. In an embodiment, such as shown in FIG. 1, power source 18 is positioned as close as possible to the first electrode 14 and may be an integral part of that first electrode 14.

As described above, patch 10 further includes a base member 20, which supports the first electrode 14, second electrode 16, and power source 18, and directly or indirectly maintains the first electrode 14 and second electrode 16 in a spaced-relation to each other to define a gap 28 therebetween. In one embodiment, the gap 28 may include a range that is greater than about 5 to about 10 mm; the gap size will depend, at least in part, on the size of the device 10. It will be noted that the minimum range of 5 to 10 mm is derived from a related embodiment, wherein the generation of an oxidizing agent is desired. It is noted, however that the configuration for generation of an oxidizing agent may be different than a configuration for wound treatment; for example for generation of an oxidizing agent, a hydrogel may occupy the interface between the two electrodes. Preferably, wherein surface wound treatment and iontophoretic dermal wound treatment are desired the gap interface between the two electrodes 28 will include hydrogel.

Preferably, a conductor (not shown in FIG. 1) couples electrodes 14, 16 to the respective terminals 24, 26 of power source 18. Examples of conductors that may couple electrodes 14, 16 to power source 18 include, but are not limited to wiring (flat or round), conductive ink, conductive adhesive, printed connection means, soldered connection means, connection means attached by UV, glued connection means, conductive EVA welding, and/or combinations thereof.

While the embodiment of FIG. 1 illustrates circular electrodes 14, 16 and a circular power source 18, other shapes of electrodes and power sources may be used without departing from the scope of the invention. FIG. 1 shows a concentric arrangement of electrode 14, 16, with a central electrode 14 and a peripheral electrode 16. FIG. 1 illustrates only one possible arrangement of electrodes and battery on a base member, other arrangements, may be used without departing from the scope of the invention. In FIG. 1, both electrodes 14, 16 are coated with hydrogel 30, which readily facilitates providing a moist surface and in addition a conductive interface means between the patch and body area of a subject. Optionally, hydrogel 30 may contain a pharmaceutically active agent. As indicated, a hydrogel may be thought of as an example of a moist surface as well as an example of a conductive interface. It is noted that a conductive interface may also be a conductive adhesive, whereas a moist surface, as used in connection with the wound healing devices/patches described herein, is preferably not a conductive adhesive.

In an alternative embodiment, wherein device 10 is part of a kit, hydrogel 30 may not be pre-coated onto the electrodes. In such a kit, the hydrogel may be supplied separately and can be administered in any suitable way, such as, but not limited to applying directly onto the electrodes via loading holes prior to use of device 10, or alternatively applying directly onto the wound.

Base member 20 may optionally be manufactured from any suitable material, which can accommodate the wound treatment patch components. Suitable materials include, but are not limited to woven material, non-woven material, polymers, conducting material, non-conducting material, paper, cardboard, plastic, synthetic materials, natural materials, fabric, metals, wood, glass, Perspex, or a combination thereof. Preferably, the material of base member is a non-conductive material. More preferably, base member is made from polyester. Optionally, base member 20 can be made up of a plurality of materials, which can be stacked or connected in a co-planar way by any suitable attachment means. Preferably, base member 20 is made up of one continuous piece of material.

According to a preferred embodiment of the present invention, power source 18 may be an electrochemical cell. In a preferred embodiment, power source 18 may be thin and flexible. In one embodiment, power source 18 may be disposable. In an alternative embodiment, power source 18 may be rechargeable.

Figure 2:
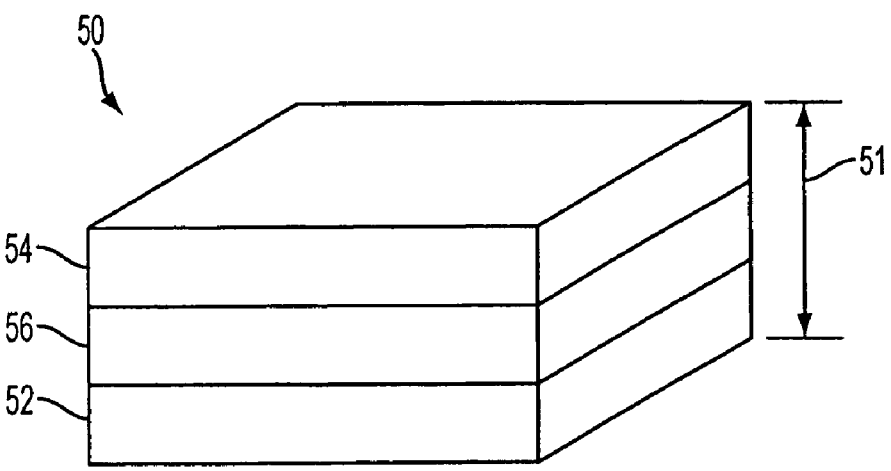
FIG. 2 illustrates a schematic representation of an exemplary power source in accordance with an embodiment of the invention.

FIG. 2 illustrates a schematic representation of an exemplary power source 50 in accordance with an embodiment of the invention. Preferably, power source 50 is thin and flexible. The term "power source" as used herein includes, but is not limited to, any suitable cell in which chemical energy is converted to electric energy by a spontaneous electron transfer reaction. The term includes cells with non-spontaneous reactions, galvanic cells, electrolytic cells, and/or a combination thereof. In the embodiment of FIG. 2, the power source is depicted as an electrochemical cell. The thickness 51 of the electrochemical cell 50 may be up to 4 mm, more preferably up to 2 mm and most preferably up to 1 mm. In a presently preferred embodiment, electrochemical cell 50 includes a positive pole layer 52, a negative pole layer 54, and an electrolyte layer 56 interposed therebetween. By way of example, a suitable electrochemical cell 50 is described in U.S. Pat. Nos. 5,652,043, 5,897,522, and 5,811,204, each of which are incorporated herein by reference in their entireties. Briefly, the electrochemical cell described in the above-identified U.S. Patents is an open liquid state, electrochemical cell, which can be used as a primary or rechargeable power source for various miniaturized and portable electrically powered devices of compact design. In one embodiment, a preferable electrochemical cell 50 may comprise a first layer of insoluble negative pole 54, a second layer of insoluble positive pole 52, and a third layer of aqueous electrolyte 56 disposed between the first 54 and second 52 layers and may include (a) a deliquescent material (not shown) for keeping the open cell wet at all times; (b) an electroactive soluble material (not shown) for obtaining required ionic conductivity; and, (c) a water-soluble polymer (not shown) for obtaining a required viscosity for adhering the first and second layers to the third layer.

Yet, in another preferred embodiment, an electrochemical cell may comprise a plurality of self-contained, serially connected galvanic power sources, as described for example in U.S. Pat. No. 6,421,561, which is incorporated herein by reference in its entirety. Several preferred embodiments of the disclosed electrochemical cell include (i) engaging the electrolyte layer in a porous substance, such as, but not limited to, a filter paper, a plastic membrane, a cellulose membrane and a cloth; (ii) having the first layer of insoluble positive pole include manganese-dioxide powder and the second layer of insoluble negative pole include zinc powder; (iii) having the first layer of insoluble negative pole and/or the second layer of insoluble positive pole further include carbon powder; (iv) selecting the electroactive soluble from zinc-chloride, zinc-bromide, zinc-fluoride and potassium-hydroxide; (v) having the first layer of insoluble negative pole include silver-oxide powder and the second layer of insoluble positive pole include zinc powder and the electroactive soluble material is potassium-hydroxide; (vi) having the first layer of insoluble negative pole include cadmium powder and the second layer of insoluble positive pole include nickel-oxide powder and selecting the electroactive soluble material to be potassium-hydroxide; (vii) having the first layer of insoluble negative pole include iron powder and the second layer of insoluble positive pole include nickel-oxide powder and selecting the electroactive soluble material to be potassium-hydroxide; (viii) having the first layer of insoluble negative pole and the second layer, of insoluble positive pole include lead-oxide powder, then cell is charged by voltage applied to the poles and the electroactive soluble material is selected in this case to be sulfuric-acid; (ix) the deliquescent material and the electroactive soluble material can, be the same material such as zinc-chloride, zinc-bromide, zinc-fluoride and potassium-hydroxide; (x) the deliquescent material is selected from the group consisting of calcium-bromide, potassium-biphosphate and potassium-acetate; (xi) the water-soluble polymer can be polyvinyl alcohol, polyacrylamide, polyacrylic acid, polyvinylpyrolidone, polyethylenoxide, agar, agarose, starch, hydroxycthylcellulose and combinations and copolymers thereof; (xii) the water-soluble polymer and the deliquescent material can be the same material such as dextrane, dextranesulfate and combinations and copolymer thereof. An electrochemical cell may preferably incorporate any one or more of the embodiments described above. Preferred configurations for electrochemical cells according to the present invention involve those combinations, which are devoid of poisonous compounds.

Preferably, the power source is applied using a suitable printing technique.

A preferred power source, such as power source 18, FIG. 1, provides a direct current electrical potential (voltage) in the range between about 0.5V and about 20V. Such electrical potential can be supplied by a single electrochemical cell or a number of electrochemical cells, linked together, to afford the desirable voltage. Preferably, the current and or voltage supplied by a power source is fixed and cannot be adjusted by a user; where a user may include, but is not limited to the patient or subject of wound treatment or an individual administering the treatment. In yet another embodiment, the electrical potential may be adjusted, to satisfy at least one of the following criteria:

The voltage may be adjusted to enable an iontophoretic delivery of an active substance into the wound or area surrounding the wound. For that purpose, voltage may be adjusted to provide an electrical current of between about 0.002 mA/cm$^2$ and 10 mA/cm$^2$.

The voltage may be adjusted to minimize irritation, which may result from excessive electrical current, passing into and through the skin. Thus, in a preferred embodiment, the voltage may be adjustable and may be adjusted within a range between about 0.5V and about 20V; and in a more preferred embodiment, the voltage may be adjustable and may be adjusted within a range between about 1V and about 4.5V. In a preferred embodiment, any adjustment may be made through automatic mechanisms, such as sensors. In the case of an alternating or pulsed electrical current, the output may be adjusted for optimal voltage, current and current profile (frequency, amplitude and wave shape), according to the nature and severity of the condition.

The final current may optionally be adjusted using a DC-DC electronic converter. In the case of an alternating or pulsed electrical current, the output may be produced using a DC-AC electronic converter.

Optionally, power source may be a single electrochemical cell. However, power source need not be limited to one cell, but may include a plurality of connected electrochemical cells, a plurality of batteries, and/or electronics configured to increase, control, and change phase of the supplied electric current and wherein the power supply is thin and flexible. Electrochemical cell in device preferably provides electrical potential (voltage) to the desired body area of the subject.

The power supply may optionally be located in any suitable position on the device.

A power supply to the device may provide a duty cycle and pulse repetition rate of between about 1% and about 99%. The frequency of the power supply may preferably be from about 1 Hz to about 1000 Hz. The power supply may provide voltage in a range of from about 0.2V to about 100V to the device.

Returning now to FIG. 1, electrodes 14, 16 may be formed of a conductive material. Preferably, electrodes 14, 16 are formed from a metal, e.g., a metal foil or metal deposited or painted on a suitable backing. Electrodes 14, 16 may be applied to the device by, for example, a suitable printing technology such as, but not limited to, silk print, offset print, jet printing, lamination, materials evaporation or powder dispersion.

Preferably, the electrode 14, 16 is made from a metal, which is effective in the treatment of wounds. In one preferred embodiment, at least one of electrodes 14, 16 comprises silver metal. Generated silver ions can be used therapeutically in wound treatment. In a further preferred embodiment, at least one electrode 14, 16 comprises both silver and silver chloride. Yet, in another preferred embodiment, at least one of the electrodes 14, 16 comprises carbon or graphite.

In yet another preferred embodiment, at least one of the electrodes 14, 16 comprises zinc. Zinc ions generated in-situ from a zinc electrode can readily be delivered iontophoretically by device 10 into a wound.

Zinc ions can accelerate recovery of many types of wounds including burns. Oral administration of zinc is not effective in wound treatment and due to the susceptibility of zinc to oxidation, topical application of zinc, in for example an ointment, has a very limited effect. Therefore, zinc ions generated from a zinc electrode of device 10 offers an improved method of wound treatment with zinc. The properties of zinc ions facilitate their effective use in treatment of wounds. Zinc has a direct anti-microorganism effect (anti-bacterial, anti-fungal and anti-viral), which is effective in surface wound treatment and deep wound treatment. In addition, zinc has an indirect anti-microorganism effect, by augmenting antigen specific immunity. Further, zinc has an anti-inflammatory effect, acting on mast cells and basophils, reducing histamine release and tissue damage. Zinc also accelerates epithelial growth. The biological effects of zinc can be combined with its skin moistening effect. Still further, zinc ions can be used as a driving force for delivering other drugs, such as but not limited to water soluble drugs, uncharged drugs and hydrophobic drugs using for example C.D. (cyclodextrin) into the wound by an electroosmotic mechanism. Driving force is proportional to current. A zinc electrode can readily facilitate relatively high current and therefore with relatively low voltage the zinc can act as a significant driving force for delivery of other drugs.

Other examples of suitable metals for electrodes include copper, manganese dioxide, aluminum, platinum, stainless steel, gold, titanium, or a combination thereof. Alternatively, electrodes may be formed of a hydrophobic polymer matrix containing a conductive filler such as a metal powder/flakes, powdered graphite, carbon fibers, or other known electrically conductive filler material. Any other conductive element or compound, including metal and non-metal materials, can be incorporated into the material of the electrodes 14, 16. In an embodiment, the electrodes 14, 16 may be provided as thin sheets coupled to the power source 18, or may be printed onto the base member 20 in spaced relation to each other to define the gap 28 therebetween. Preferably, at least one electrode is an active electrode and at least one electrode is a counter electrode. Optionally, the active electrode can be the cathode or anode or both the cathode and the anode. Defining which electrode is the active electrode is preferably dependent on the charge of the composition (e.g., formulation or pharmaceutical wound treatment agent) being used.

Optionally, the electrode 14, 16 area can be continuous, or formed in any shape or configuration. Optionally, each electrode 14, 16 may not have the same shape and/or same area.

Optionally, electrodes 14, 16 may be in any suitable conformation in relation to each other including but not limited to a coplanar and cofacial arrangement. Preferably, electrodes 14, 16 are in a conformation, which readily facilitates diffuse area treatment. Preferably, electrodes 14, 16 are configured to provide surface treatment and/or dermal treatment of the wound area. Preferred electrode configurations include, but are not limited to concentric configuration, bilateral configuration and labyrinth configuration.

Optionally, patch 10 can include a plurality of electrodes 14, 16, comprised of equal or unequal numbers of anodes and cathodes. Such a multi-electrode patch facilitates providing simultaneously a plurality of treatments in different areas with one composition or a plurality of compositions in different body areas or the same body area.

Preferably, the device of the present invention provides electrical stimulation to the wound area and surrounding area. Electrical stimulation is important in the treatment of wounds. It is useful to reduce congestion in and around the wounded tissues, increasing circulation, generating motor and sensory stimulation and peripheral nerve stimulation.

Sensory stimulation of muscle allows for pain control. Micro-amp stimulation can lead to electro-analgesia, which can typically occur after several minutes following application of the device of the present invention. Motor stimulation can be implemented for stimulating acupuncture points, for creating muscle tetany to assist in breaking the pain-spasm cycle, for muscle re-education, prevention of disuse atrophy and for wound healing. The monophasic pulse allows for a temporary accumulation of electrical charge in stimulated tissue, which is thought to be responsible for cell regeneration in conditions such as open wounds, local bacterial infections and non-union fractures.

Thus electric stimulation resulting from the device of the present invention augments the endogenous current flow, allowing cells in the traumatized area to regain their capacitance. Resistance is reduced, allowing bioelectricity to flow through and reestablish homeostasis. This process helps to initiate and perpetuate the many biochemical reactions that occur in healing. Muscular spasm, occurring as a reaction to trauma, causes reduction in blood supply, resulting in local hypoxia, accumulation of noxious metabolites, and pain. This, in turn, leads to reduction of ATP synthesis. Thus, MET (muscle energy technique) stimulation results in replenishment of ATP. In addition, electrical stimulation of a wound increases the concentration of growth factor receptors, which increases collagen formation. This is important in view of the hypothesis that a major mechanism in causing ulceration is removal of growth factors by venous hypertension.

Current polarity of the electrical stimulation resulting from device 10 of the present invention can optionally be selected according to the specific type of wound and location of the wound. Negative current (cathode) may be more beneficial for effecting certain types of bone and nerve repair. Positive (anodal) current may be more effective in certain types of skin lesion treatment.

Preferably, the device 10 includes an interfacing layer 30. Preferably, the interfacing layer 30 between the patch 10 and the skin is a moist conductive layer. Preferably, the moist conductive layer has two principal functions: (1) to provide a moist surface, having the therapeutic benefits as detailed in the background of this application; and (2) to conduct electrical current, which also exerts healing benefits, as also laid out in the background section of the present invention. By combining the benefits of the moist surface and the electrical current, a synergistic effect is conceivably attained.

Without derogating from the generality of optional interfacing materials 30, one example is a conductive hydrogel. A hydrogel is a polymer swollen in water. A polymer gel is an essentially infinite molecule composed of long polymer chains connected by crosslinks.

Typically, the hydrogel is composed of water, a gelling agent, a hydrophilic solvent (also termed "humectant") and an electrolyte. Hydrogels may have different characteristics, such as water content, gelling agents, electrolyte content and pH, which can be controlled in order to attain favorable wound care capabilities. Any suitable hydrogel may be used including hydrogels disclosed in U.S. patent application No. 20040028739 to Rippon et al.

Optionally, the moist conductive layer 30 can include an active drug and as such act as a drug reservoir.

Figure 3A:
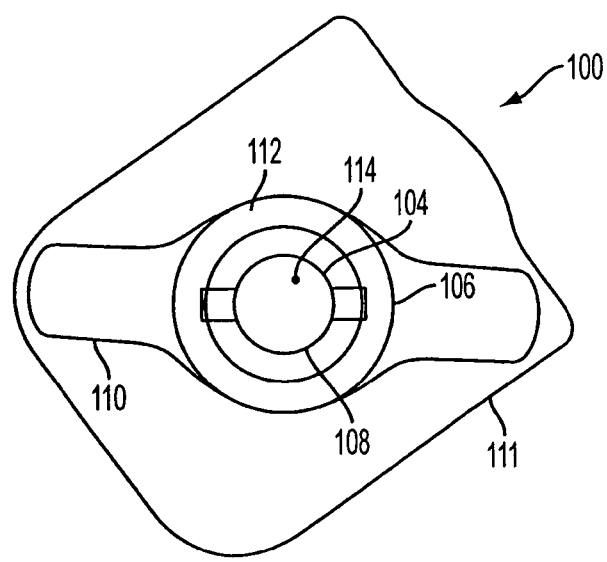
FIG. 3A is a schematic representation of a wound treatment device according to an alternative embodiment of the present invention.
Figure 3B:
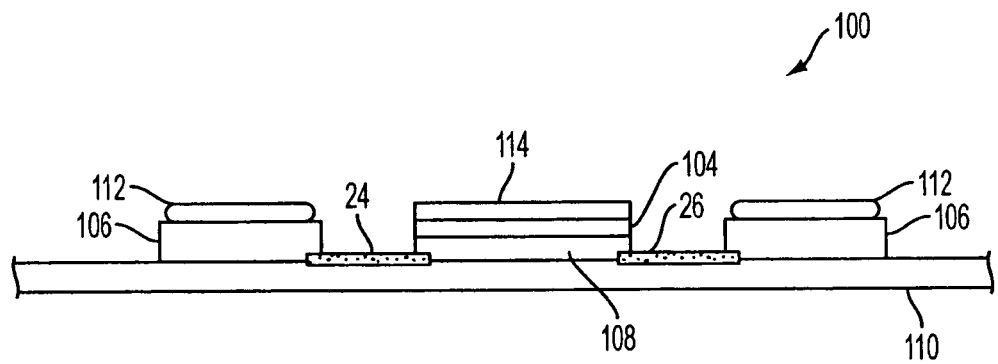
FIG. 3B provides one example of a schematic cross-sectional view of a wound treatment device in accordance with an embodiment of the present invention.

FIG. 3 shows an alternative embodiment of a device/patch for wound treatment 100 according to the present invention. It is noted that reference to FIG. 3 includes reference to both FIGS. 3A and 3B, unless otherwise noted. Preferably, patch 100 is a flexible, wearable patch 100 that can conform and adhere to the skin surface of a person. The patch 100 further includes at least one first electrode 104, identified as "anode", at least one second electrode 106, identified as "cathode" and at least one power source 108, supported on a base member 110 in spaced relation to each other to define a gap therebetween. While the first electrode 104 may be identified as an anode and the second electrode 106 may be identified as a cathode, those of skill will recognize that these designations may be reversed. In the embodiment as illustrated, the base member 110 rests on a release liner 111. Patch 100 may be provided with an adhesive (not shown) (similar to 22 of FIG. 1), that facilitates patch 100 adhering to the wound or surrounding skin/tissue. Alternative attachment means are possible.

Patch 100 is equipped with a thin power source 108, which, according to certain preferred embodiments, produces direct current (galvanic current), and according to other embodiments, produces an alternating or pulsed electrical current. The choice between direct current and alternating or pulsed current is made according to the nature and severity of the injury and the involvement of pain in the condition.

The device 100 may be of any suitable size and shape, which is effective for use in wound treatment. FIG. 3 shows one non-limiting example of a round device, with peripheral electrode 106 and central electrode 104. The width of the device can vary from less than about 1 cm to about 20 cm and the length of the device can range from about 2 cm to about 30 cm. Smaller or larger dimensions are possible. The device 100 is preferably fabricated from thin and flexible materials, which enable at least those surfaces that contact a patients skin to conform to the contours of the patient when the device 100 is applied thereon.

The components of device 100 are substantially as described hereinabove for device 10 in FIG. 1. Device 100 includes a hydrogel 112 moist surface, which is preferably coated onto the peripheral electrode 106. Device 100 further includes a substrate 114, which is disposed onto the central electrode 104. In an alternative embodiment a moist surface, such as, hydrogel can optionally be coated onto central electrode 104 and substrate can be disposed onto peripheral electrode 106. In such an embodiment as shown in FIG. 3, at least one of the moist surfaces comprises an absorbing substrate and a conductive carrier, which may be gel, cream or lotion. Preferably, substrate 114 is capable of absorbing the conductive carrier.

In a preferred alternative embodiment, substrate 114 includes a porous and/or absorbent material for retaining a formulation. Preferably, substrate 114 is interposed between at least one of the electrodes 104, 106 and the subject's skin and, upon application of current to electrode 104, 106; patch 100 can deliver electrical current to the subject's skin. One example of such a substrate 114 retaining a formulation including an active substance would be a soaked pad.

By way of illustration, FIG. 3B provides one example of a schematic cross-sectional view of a wound treatment device 100 in accordance with an embodiment of the present invention. The schematic cross-sectional view of the wound treatment device 100 is generally representative of cross-sectional views of each of the embodiments illustrated herein. The description of the components of the device 100 as shown in FIG. 3B is as described above in FIGS. 1-3A.

Preferably, the gel may comprise water, a gelling agent and other excipients, known to those skilled in the art of pharmaceutical formulations. Gelling agents may include polymers, such as (1) polyacrylate and polyacrylate co-polymer resins, e.g., poly-acrylic acid and poly-acrylic acid/methacrylic acid resins such as known and commercially available under the trade name Carbopol (see Fiedler at 254-256), in particular the products Carbopol 934, 940 and 941, and Eudragit (see Fiedler at 486-487), in particular the products Eudragit E, L, S, RL and RS and, most especially, the products Eudragit E, L and S; (2) celluloses and cellulose derivatives including: alkyl celluloses, e.g. methyl-, ethyl- and propyl-celluloses; hydroxyalkyl-celluloses, e.g. hydroxypropyl-celluloses and hydroxypropylalkyl-celluloses such as hydroxypropyl-methyl-celluloses; acylated celluloses, e.g. cellulose-acetates, cellulose-acetatephthallates, cellulose-acetatesuccinates and hydroxypropylmethyl-cellulose phthallates; and salts thereof such as sodium-carboxymethyl-celluloses. Examples of such products suitable for use in accordance with the present invention are those known and commercially available, e.g. under the trade names Kiucel and Methocel (see Fiedler at 688 and 790), in particular the products Klucel LF, MF, GF and EF and Kethocel K 100, K 15, K 100M, E 5M, E 15, E 15M and E 100M; (3) polyvinylpyrrolidones, including for example poly-N-inylpyrrolidones and sinylpyrrolidone co-polymers such as vinylpyrrolidone-vinylacetate co-polymers. Examples of such compounds suitable for use in accordance with-the present invention are those known and commercially available, e.g. under the trade name Kollidon (or, in the USA, Povidone) (see Fiedler at 694-696), in particular the products Kollidon 30 and 90; (4) polyvinyl resins, e.g. including polyvinylacetates and alcohols, as well as other polymeric materials including gum traganth, gum arabicum, alginates, e.g. alginic acid, and salts thereof, e.g. sodium alginates; and (5) inorganic thickening agents such as atapulgite, bentonite and silicates including hydrophilic silicon dioxide products, e.g. alkylated (for example methylated) silica gels, in particular colloidal silicon dioxide products as known and commercially available under the trade name Aerosil (see *Handbook of Pharmaceutical Excipients*, 253-

256 (Raymond C. Rowe ed., Pharmaceutical Press)) in particular the products Aerosil 130, 200, 300, 380, 0, OX 50, TT 600, MOX 80, MOX 170, LK 84 and the methylated Aerosil R 972.

Preferably, the hydrogel and/or the gel possess high electrical conductivity. By way of comparison, hydrogels used as a conductive interface, preferably have an impedance less than about 150 Ohms.

In a particularly preferred embodiment, the hydrogel or gel (also termed "composition") of the present invention comprises a safe and effective amount of one or more active ingredients (also termed "active agent" and "drug") or pharmaceutically acceptable salts thereof. By combining the benefits of (1) moist surface; (2) electrical current; and (3) effective amount of one or more active ingredients; a synergistic effect may be attained.

The term "safe and effective amount" as used herein, means an amount of an active ingredient high enough to modify the wound condition to be treated or to deliver the desired skin benefit, but low enough to avoid serious side effects, at a reasonable benefit to risk ratio within the scope of sound medical judgment. What is a safe and effective amount of the active ingredient will vary with the specific active, the ability of the active to penetrate through the skin, the age, health condition, and skin condition of the user, and other like factors.

The term "pharmaceutically-acceptable salts" as used herein may refer to any of the commonly-used salts that are suitable for use in contact with the tissues of humans without undue toxicity, irritation, incompatibility, instability, irritation, allergic response, and the like.

Typically, the actives of the present invention comprise more than about 0.001% and less than about 50%, preferably from about 0.01% to about 10%, by weight of the composition. Lower percentages and higher percentages are possible with the present invention. When using growth factors in the device of the present invention, lower percentages are more preferable.

Optional active ingredients, which may be used with the device of the present invention include, but are not limited to non-steroidal anti-inflammatory agents, topical anesthetics, antimicrobial and anti-fungal agents, oxidizing agents, zinc, silver, active agents for tissue growth, growth factors, antiviral agents, herbal and natural remedies and any combination thereof as detailed below:

Non-Steroidal Anti-Inflammatory Actives (NSAIDS)

Examples of NSAIDS include, but are not limited to the following categories: propionic acid derivatives; acetic acid derivatives; fenamic acid derivatives; biphenylcarboxylic acid derivatives; and oxicams. All of these NSADS are fully described in the U.S. Pat. No. 4,985,459 to Sunshine et al., issued Jan. 15, 1991, and incorporated by reference herein. Examples of useful NSAIDS include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, mniroprofen, tioxaprofen, suprofen, alminoprofen, tiaprofenic acid, fluprofen and bucloxic acid. Also useful are the steroidal anti-inflammatory drugs including hydrocortisone and the like.

Topical Anesthetics

Examples of topical anesthetic drugs include, but are not limited to benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Antimicrobial and Antifungal Actives

Examples of antimicrobial and antifungal actives include, but are not limited to beta-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate and clotrimazole.

Oxidizing Agents

Oxidizing agents are useful in the treatment of wounds. Examples of such oxidizing agents include, but are not limited to oxygen; peroxides, such as hydrogen peroxide and benzoyl peroxide; elemental halogen species; such as iodine and iodine-povidone; as well as oxygenated halogen species, such as hypochlorite ions and perchlorite species and zinc ions. Organic oxidizing agents are also included in the definition of "oxidizing agent" according to the present invention, such as quinones.

Yet, in a preferred embodiment, the oxidizing agents are produced in-situ from a precursor, upon closure of an electrical circuit. Still in another preferred embodiment, the oxidizing agent is produced by an electrochemical redox process, upon closure of an electrical circuit. Examples of such redox processes, yielding oxidizing agents are presented below:

| Precursor | Oxidizing agent | E° (V) |
|---|---|---|
| $I^- + 2\,OH^-$ | $IO_3^- + 3\,H_2O$ | 0.26 |
| $OH^-$ | $O_2 + 2\,H_2O$ | 0.41 |
| $2\,OH^-$ | $IO^- + H_2O$ | 0.485 |
| $2\,I^-$ | $I_2$ | 0.535 |
| $H_2O_2$ | $O_2 + 2\,H^+$ | 0.695 |
| $Cl^- + 4\,OH^-$ | $ClO_2^- + H_2O$ | 0.76 |
| $Cl^- + 2\,OH^-$ | $ClO^- + H_2O$ | 0.841 |
| $Cl^-$ | $Cl_2$ | 1.358 |
| 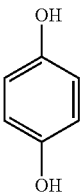 Hydroquinone | 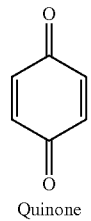 Quinone | 0.09 |

Growth Factors

Growth factors are involved in three phases of wound healing (inflammation, proliferation of cells necessary for wound closure and remodeling/restructuring of initial scar tissue)

and also have the ability to regulate many other functions within the cell, including protein synthesis. Growth factors are essential to wound healing. Their functions include, attracting useful cells and proteins to the wound, including immune cells to fight infection and other cells to form connective tissue; stimulating and increasing production of connective tissue; creating a new supply of blood vessels to nourish the site; promoting remodeling; and promoting new skin to grow across the open area of the wound. The most important growth factors involved in the process of wound healing include, but are not limited to PDGF (platelet-derived growth factor), TGF (alpha and beta), EGF (epidermal growth factor), FGF (fibroblast growth factor), KGF (keratinocyte growth factor), IL-1,2,6,8 (interleukins), INFs (interferon alpha, beta and delta and thromboxane A2.

Natural Remedies

Many natural remedies are available and have been found to have a positive effect on wound healing. Natural remedies, which may be used with the device of the present invention include, but are not limited to formulations containing aloe vera, vitamin C, vitamin E, honey, arnica, comfrey, plantain, tea tree oil, chamomile, echinocea, propolis, green tea, white oak bark, mugwart, dill, oregano, coffee, garlic, petroleum jelly or a combination thereof.

In an embodiment wherein device 100 includes a moist surface and a pharmaceutically active substance, device 100 may be configured to facilitate at least a combination of effects and a synergistic effect on wound treatment of electrical stimulation, moist wound treatment and active compound treatment.

In an alternative embodiment, wherein device 100 is part of a kit, hydrogel may optionally not be pre-coated onto the electrodes or the pharmaceutically active substance may not be coated on the substrate or contained in the moist surface, such as hydrogel. In such a kit, the moist surface, such as hydrogel and/or pharmaceutically active substance may be supplied separately and may be administered in any suitable way, such as, but not limited to applying directly onto the electrodes and/or substrate via loading holes prior to use of device 100 or alternatively applying directly onto the wound.

Figure 4:
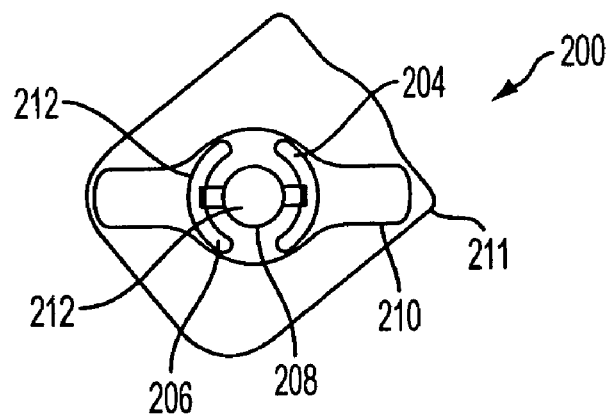
FIG. 4 is a schematic representation of a wound treatment device according to an alternative embodiment of the present invention.

FIG. 4 shows an alternative embodiment of a device/patch 200 for wound treatment according to the present invention. Preferably, patch 200 is a flexible, wearable patch 200 that can conform and adhere to the skin surface of a person. As can be seen from FIG. 4, patch 200 further includes at least one first electrode 204, identified as "anode", at least one second electrode 206, identified as "cathode" and at least one power source 208, supported on a base member 210 in spaced relation to each other to define a gap therebetween. While the first electrode 204 may be identified as an anode and the second electrode 206 may be identified as a cathode, those of skill will recognize that with direct current these designations may be reversed. In the embodiment as illustrated, the base member 210 rests on a release liner 211. Patch 200 may be provided with an adhesive (not shown) (similar to 22 of FIG. 1), that facilitates patch 200 adhering to the wound or surrounding skin/tissue. Alternative attachment means are possible. It is noted that optionally, the embodiment of FIG. 4 may include a central electrode and two peripheral electrodes. The central electrode may be disposed above the power source. In one example, the central electrode may be a cathode and the peripheral electrodes may be anodes. Of course, as noted above, these designations may be reversed.

The device 200 may be of any suitable size and shape, which is effective for use in wound treatment. FIG. 4 shows one non-limiting example of a round device, with a bilateral peripheral electrode arrangement. Electrodes 204, 206 are connected to power source 208. Power source 208, according to certain preferred embodiments, produces direct current (galvanic current), and according to other embodiments, produces an alternating or pulsed electrical current. The choice between direct current and alternating or pulsed current is made according to the nature and severity of the injury and the involvement of pain in the condition.

In FIG. 4, it can be seen that both electrodes 204, 206 are coated with a moist surface, such as, but not limited to hydrogel 212. Optionally, moist surface, such as hydrogel 212 may include an active ingredient as described hereinabove. The central area on power source 208 preferably also comprises a moist surface, such as hydrogel 212, which may optionally contain an active ingredient as described hereinabove. Optionally, the active ingredients contained in moist surface, such as hydrogel 212 coated on each of the electrodes and central power source may be different active ingredients.

The description of the components of the device 200 shown in FIG. 4, apart from the differences outlined herein, is as described above in FIGS. 1-3.

In an alternative embodiment, wherein device 200 is part of a kit, moist surface, such as hydrogel and optional active agent may optionally not be pre-coated onto the electrodes. In such a kit, the hydrogel and optional active agent are separate components and can be applied or administered in any suitable way, such as, but not limited to applying directly onto the electrodes via loading holes prior to use of device 200, or alternatively applying directly onto the wound.

Figure 5:
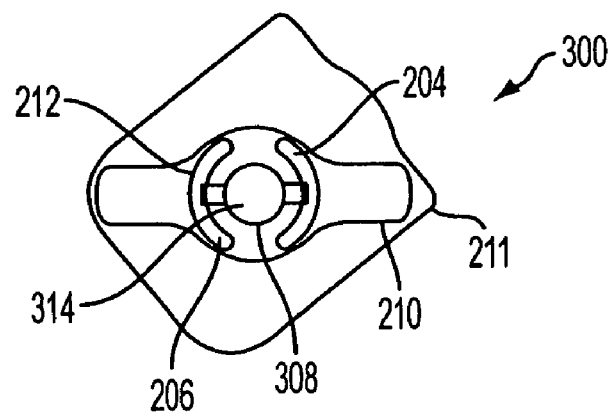
FIG. 5 is a schematic representation of a wound treatment device according to a further optional embodiment of the present invention.

FIG. 5 shows an alternative embodiment of a device/patch for wound treatment 300 according to the present invention. As can be seen from FIG. 5, device 300 is the same as FIG. 4, device 200, except that a substrate 314 is disposed on the central area of the power source 308 in device 300, wherein the substrate is capable of absorbing the conductive carrier, which may optionally be a gel, cream or lotion and which optionally may contain an active agent. It is noted that optionally, the embodiment of FIG. 5 may include a central electrode and two peripheral electrodes. The central electrode may be disposed above the power source. In one example, the central electrode may be a cathode and the peripheral electrodes may be anodes. Of course, as noted above, these designations may be reversed.

In an alternative embodiment, wherein device 300 is part of a kit, kit may include device and conductive carrier as separate components. Conductive carrier may optionally be a gel, cream or lotion and optionally may contain an active agent. Preferably, conductive carrier is a hydrogel. In such a kit, the hydrogel and optional active agent can be applied or administered in any suitable way, such as, but not limited to applying directly onto the electrodes and substrate via loading holes (not shown in FIG. 5) prior to use of device 300, or alternatively applying directly onto the wound.

Figure 6:
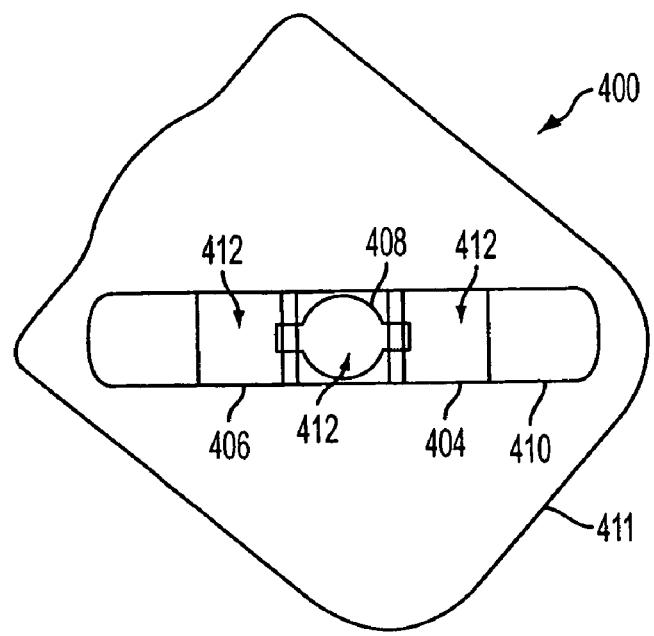
FIG. 6 is a schematic representation of a wound treatment device according to still a further embodiment of the present invention.

FIG. 6 shows an alternative embodiment of a device/patch for wound treatment 400 according to the present invention. Preferably, patch 400 is a flexible, wearable patch 400 that can conform and adhere to the skin surface of a person. As can be seen from FIG. 6, patch 400 further includes at least one first electrode 404, identified as "anode", at least one second electrode 406, identified as "cathode" and at least one power source 408, supported on a base member 410 in spaced relation to each other to define a gap therebetween. While the first electrode 404 may be identified as an anode and the second electrode 406 may be identified as a cathode, those of skill will recognize that with direct current these designations may be reversed. In the embodiment as illustrated, the base member 410 rests on a release liner 411. Patch 400 may be provided with an adhesive (not shown) (similar to 22 of FIG. 1), that facilitates patch 400 adhering to the wound or surrounding skin/tissue. Alternative attachment means are possible. It is noted that optionally, the embodiment of FIG. 6 may include a central electrode and two peripheral electrodes. The central electrode may be disposed above the power source. In one example, the central electrode may be a cathode and the peripheral electrodes may be anodes. Of course, as noted above, these designations may be reversed.

The device 400 may be of any suitable size and shape, which is effective for use in wound treatment. FIG. 6 shows one non-limiting example of a linear device, with a bilateral electrode arrangement. Electrodes 404, 406 are connected to power source 408. Power source 408, according to certain preferred embodiments, produces direct current (galvanic current), and according to other embodiments, produces an alternating or pulsed electrical current. The choice between direct current and alternating or pulsed current is made according to the nature and severity of the injury and the involvement of pain in the condition.

In FIG. 6, it can be seen that both electrodes 404, 406 are coated with moist surface, such as, but not limited to hydrogel 412. Optionally, moist surface, such as hydrogel 412 may include an active ingredient as described hereinabove. The central area on the power source 408 preferably also comprises moist surface, such as hydrogel 412, which may optionally contain an active ingredient as described hereinabove. Optionally, the active ingredients contained in hydrogel 412 coated on each of the electrodes and central power source may be different active ingredients.

In an alternative embodiment, wherein device 400 is part of a kit, moist surface, such as hydrogel and optional active agent may optionally not be pre-coated onto the electrodes. In such a kit, the hydrogel and optional active agent can be separate components and can be applied or administered in any suitable way, such as, but not limited to applying directly onto the electrodes via loading holes prior to use of device 400, or alternatively applying directly onto the wound.

The description of the components of the device 400 shown in FIG. 6, apart from the differences outlined here, is as described above in FIGS. 1-3.

Figure 7:
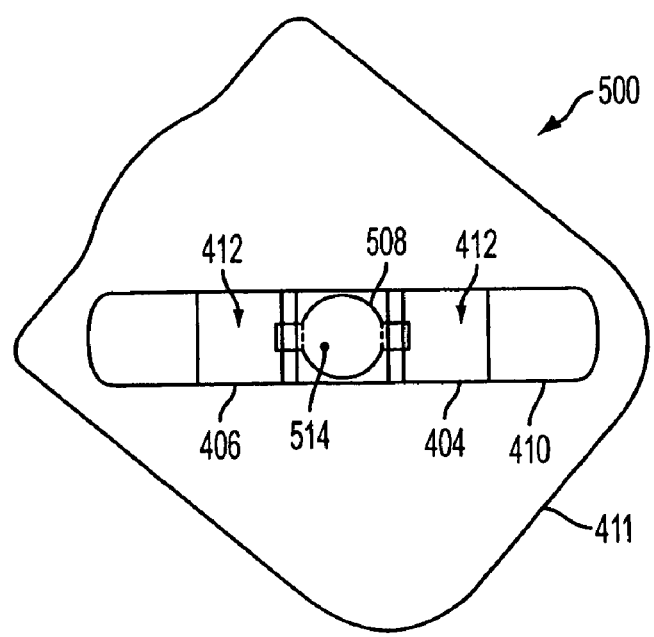
FIG. 7 is a schematic representation of a wound treatment device in a linear configuration according to an embodiment of the present invention.

FIG. 7 shows an alternative embodiment of a device/patch for wound treatment 500 according to the present invention. As can be seen from FIG. 7, device 500 is the same as FIG. 6, device 400, except that a substrate 514 is disposed on the central area of the power source 508 in device 500, wherein the substrate is capable of absorbing the conductive carrier, which may optionally be a gel, cream or lotion and which optionally may contain an active agent. It is noted that optionally, the embodiment of FIG. 7 may include a central electrode and two peripheral electrodes. The central electrode may be disposed above the power source. In one example, the central electrode may be a cathode and the peripheral electrodes may be anodes. Of course, as noted above, these designations may be reversed.

In an alternative embodiment, wherein device 500 is part of a kit, kit may include as separate components, device and a conductive carrier, which may optionally be a gel, cream or lotion and which optionally may contain an active agent. Preferably, the conductive carrier is a hydrogel. In such a kit, the hydrogel and optional active agent can be applied or administered in any suitable way, such as, but not limited to applying directly onto the electrodes and substrate via loading holes (not shown in FIG. 7) prior to use of device 500, or alternatively applying directly onto the wound.

Figure 8:
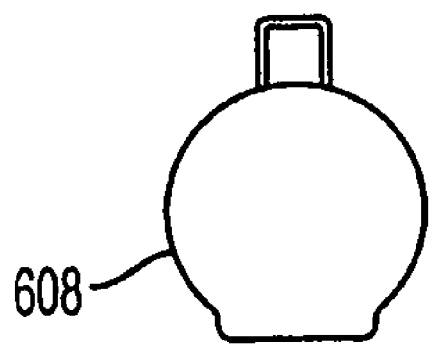
FIG. 8 is a schematic representation of an outline of a power source according to an embodiment of the present invention.

FIG. 8 is a schematic representation of an outline of a power source according to an embodiment of the present invention.

The device may be of any suitable size and shape, which is effective for use in wound treatment. One non-limiting example of a device includes a labyrinth electrode arrangement. Such a labyrinth arrangement of electrodes readily facilitates uniform current distribution. Electrodes are connected to power source 608. Power source 608, according to certain preferred embodiments, produces direct current (galvanic current), and according to other embodiments, produces an alternating or pulsed electrical current. The choice between direct current and alternating or pulsed current is made according to the nature and severity of the injury and the involvement of pain in the condition.

Device is configured to readily facilitate wound healing with current stimulation, moist surface treatment, surface treatment with zinc ions, dermal treatment with zinc ions and treatment with an optional active agent.

Figure 9:
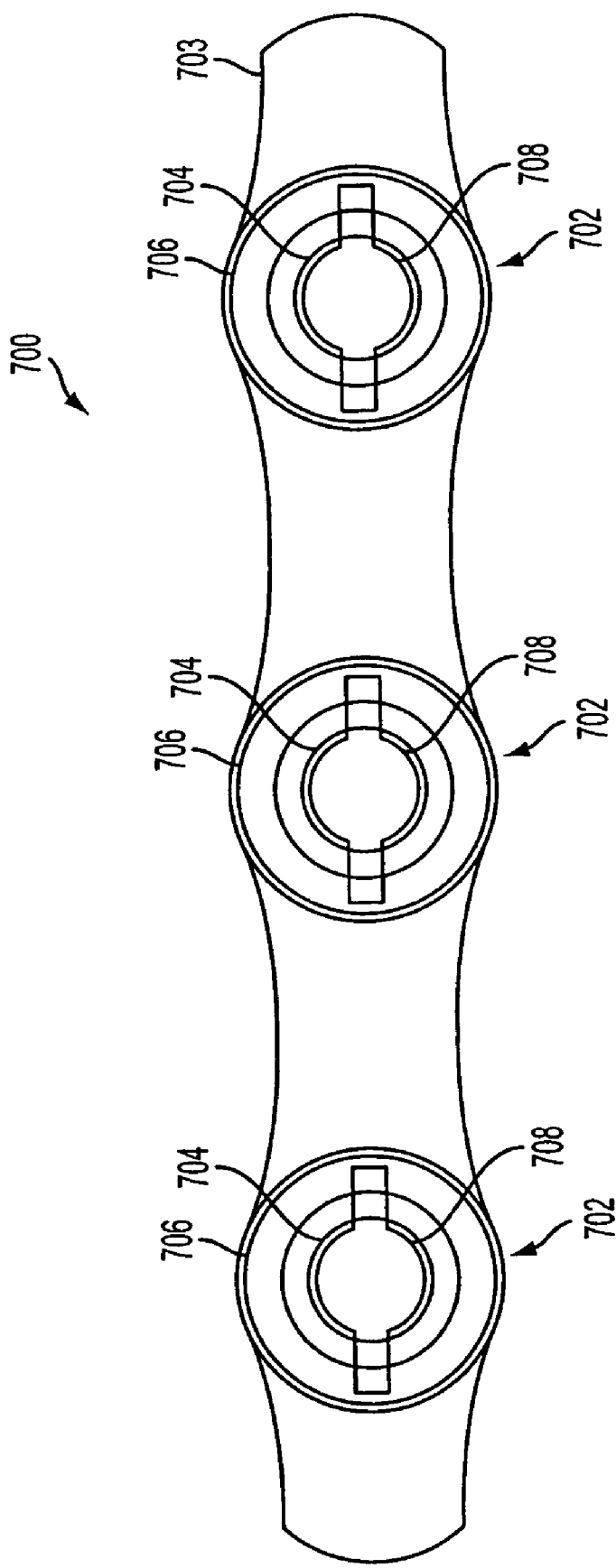
FIG. 9 is a schematic representation of a device for wound treatment according to an embodiment of the present invention, wherein the device includes a plurality of electrically operated devices.

FIG. 9 shows an embodiment of a device for wound treatment 700 of the present invention, wherein the device 700 includes a plurality of electrically operated devices 702 disposed on a base member substrate 703. As can be seen from FIG. 8, device includes 3 electrically operated devices 702. The device can optionally include any suitable number of electrically operated devices 702. Each electrically operated device 702 can optionally include the same or a different arrangement of electrodes 704, 706, and power source 708 such as one device can optionally be a linear device, one device 702 can be a circular device with bilateral electrode arrangement or one device 702 can have a concentric electrode arrangement. Such a device 700 readily facilitates providing an effect on a greater surface area than a single electrode system device. Each of the plurality of electrically operated devices 702 may optionally include a different or the same optional active agent. Each of the plurality of electrically operated devices may optionally include a moist surface. Each of the plurality of electrically operated devices may optionally include any combination of moist surface and/or absorbing substrate and/or active substance.

Figure 10:
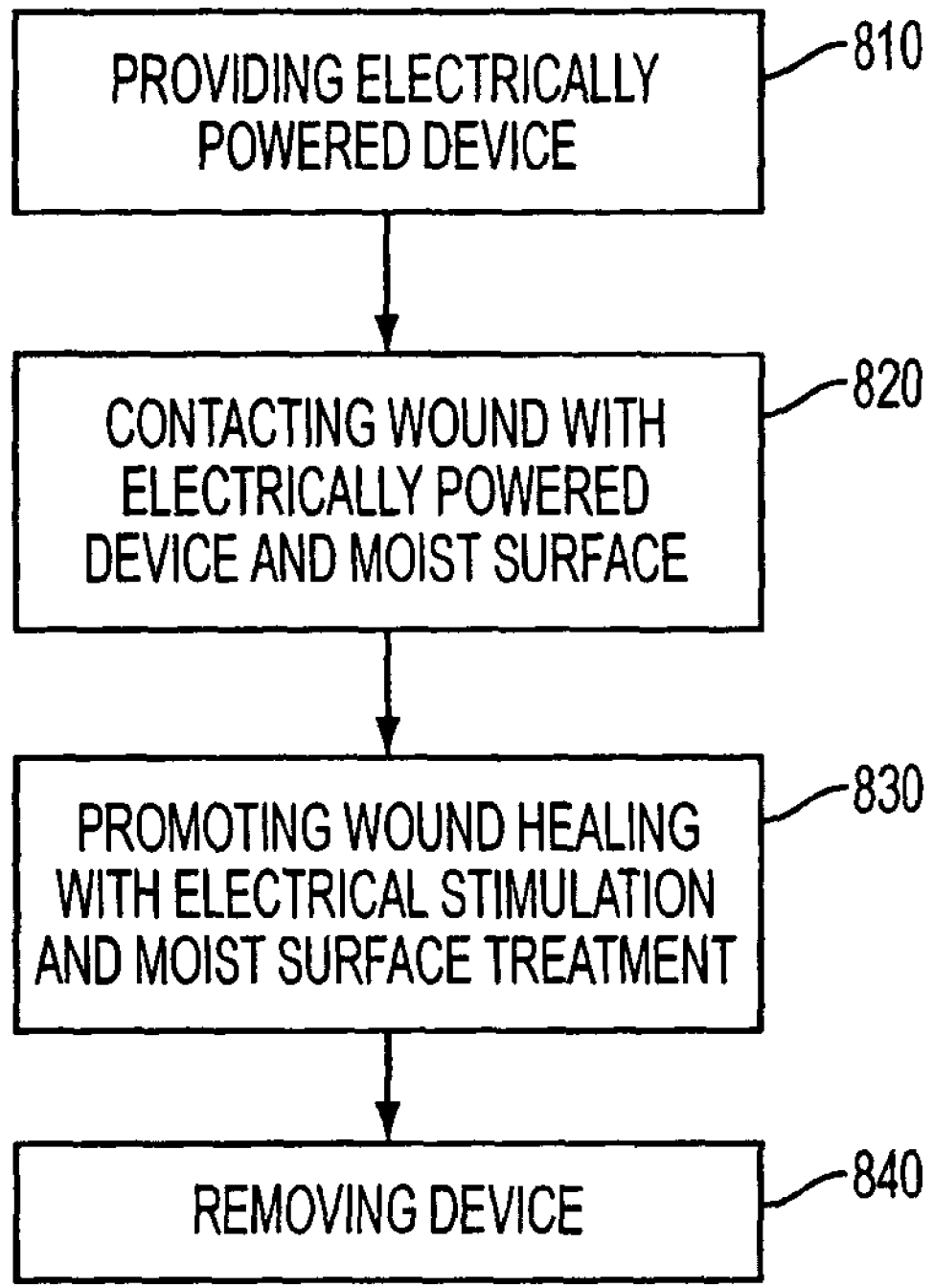
FIG. 10 is a flow diagram of a method of use of a wound treatment device according to an embodiment of the present invention.

FIG. 10 is a flow chart according to embodiments of the present invention. The flowchart applies to a method using a fully integrated patch device, or to a method using a kit including a patch device. An electrically powered device, such as a patch may be provided 810. Preferably, the electrically powered device includes at least one first electrode, and at least one second electrode and at least one power source, supported on a base member in spaced relation to each other to define a gap therebetween. The patch may be configured to facilitate providing an electrical current.

The subject may contact an affected wound area with the electrically powered device and moist surface and optional additional active substance 820. In an embodiment wherein the patch is part of a kit, the hydrogel and optional active substance may optionally be coated or loaded in any suitable way onto the electrodes and/or substrate or alternatively or in addition can be administered directly onto the wound area. In an alternative embodiment electrically powered device is used alone without a moist surface to provide wound healing only through electrical stimulation. Preferably, electrically powered device is a thin and flexible device, which conforms with the contours of the body and which includes attachment means, for ready attachment to the wound area and/or surrounding area.

Preferably, the subject promotes wound treatment with electrical stimulation and promotes wound healing with the moist surface 830. When device includes active substance, electrical stimulation preferably facilitates delivery of the active substance to exert its therapeutic effect.

The device is removed from the body area at the end of treatment time 840. Time of treatment can vary. The device is preferably removed from contact with the wound and/or wound area after a time period, which can optionally be predetermined or is determined according to the time it takes for the electrode to be depleted, or for the moist surface or active substance to be depleted. Alternatively, the device is contacted with the wound until sufficient therapeutic effect, such as the wound has healed or no more improvement can be seen.

The treatment can optionally be a one-time treatment or can be repeated in suitable time intervals any suitable number of times.

Therefore, according to one embodiment, the kit can be used sequentially, whereby the moist substance, such as but not limited to hydrogel and active agent may be first applied, followed by application of the patch. Yet, according to another embodiment of the same invention, the moist substance and optional active agent is located on a stand alone device, which may be applied simultaneously with application of the device on the target area of the skin.

Those skilled in the art can appreciate from the foregoing description that the broad techniques of the embodiments of the present invention can be implemented in a variety of forms. Therefore, while the embodiments of this invention have been described in connection with particular examples thereof, the true scope of the embodiments of the invention should not be so limited since other modifications will become apparent to the skilled practitioner upon a study of the drawings, specification, and following claims.

What is claimed is:

1. A device for treatment of a wound comprising at least one electrically powered patch comprising:
    at least one active electrode;
    at least one counter electrode;
    at least one power source electrically coupled to the at least one active electrode and at least one counter electrode; and
    at least one moist treatment surface disposed on at least one of the at least one active electrode, the at least one counter electrode and the power source, wherein the moist treatment surface is not a conductive adhesive and wherein the characteristics of the moist treatment surface are controlled in order to attain favorable wound care capabilities,
    wherein the at least one active electrode and at least one counter electrode are configured to provide surface treatment of the wound and/or dermal treatment of the wound, and
    wherein the at least one active electrode and at least one counter electrode are in a concentric arrangement with the at least one active electrode and at least one counter electrode being substantially circular, or in a bilateral peripheral arrangement with the at least one active electrode and at least one counter electrode being curvilinear.

2. The device of claim 1, wherein the characteristics of the at least one moist treatment surface are selected from the group consisting of water content, gelling agents, electrolyte content and pH.

3. The device of claim 1, further comprising a conductive interfacing layer between the patch and skin.

4. The device of claim 3, wherein the at least one moist treatment surface is the conductive interfacing layer.

5. The device of claim 1, wherein the at least one moist treatment surface comprises a hydrogel with wound care capabilities.

6. The device of claim 1, wherein the at least one moist treatment surface is selected from the group consisting of hydrogel, gel, absorbing substrate and a conductive carrier.

7. The device of claim 6, wherein the hydrogel comprises water, a gelling agent a hydrophilic solvent and an electrolyte.

8. The device of claim 1, further comprising a base member substrate.

9. The device of claim 1, wherein the at least one moist treatment surface is pre-applied to at least one of the group consisting of, both the at least one active and at least one counter electrodes, the at least one active electrode, the at least one power source, an interface area between electrodes, a central area above the at least one power source and a combination thereof.

10. The device of claim 1 further comprising an absorbent substrate attached to the at least one counter electrode, wherein the at least one active electrode is peripheral to the at least one counter electrode, and wherein the at least one counter electrode is configured to readily remove excess fluids from the wound to be absorbed by the absorbent substrate.

11. The device of claim 1 fabricated from thin and flexible materials to enable at least those surfaces that contact a patient skin to conform to the contour of the patient.

12. The device of claim 1, wherein the at least one power source is thin and flexible.

13. The device of claim 1 for treating a wound selected from the group consisting of superficial injuries, cuts, abrasions, blisters, lacerations, superficial burns, pressure sores, road rash, carpet burns, scrapes, sun burns, friction burns, pressure ulcers, stasis ulcers, diabetic ulcers, foot ulcers, post-surgical wounds, scarring, trauma wounds and a combination thereof.

14. The device of claim 1, wherein the favourable wound healing capabilities of at least one moist treatment surface are selected from the group consisting of preventing dehydration of wound surface, rehydrating wound bed, softening necrotic tissue, moisturizing effect, reduction of wound pain, cooling effect, absorption of fluid, protection from extraneous materials and microorganisms, protection from surface pressure and a combination thereof.

15. The device of claim 1, wherein the device provides a synergistic effect of the at least one moist treatment surface and electrical current on wound healing.

16. The device of claim 1, further comprising a substrate layer attached to at least one of the electrodes, configured to accommodate a formulation comprising an active agent and a conductive fluid.

17. The device of claim 1, further comprising an active agent effective in wound treatment.

18. The device of claim 1, wherein the at least one active electrode, the at least one power source, and the at least one counter electrode are printed on a substrate layer.

19. The device of claim 1, wherein the at least one moist surface is printed on the electrically powered patch.

20. The device of claim 1, further comprising attachment means.

21. The device of claim 1, comprising a plurality of electrically operated patches disposed on a single substrate base layer for treating a plurality of wounds or areas on a wound.

22. The device of claim 1, wherein the at least one active electrode comprises a metal which is effective in the treatment of wounds.

23. The device of claim 22, wherein the metal is selected from the group consisting of silver and zinc, and wherein generated ions from the metal electrode are effective in wound treatment.

24. The device of claim 23 wherein the zinc ions are generated in situ.

25. A kit for treatment of a wound comprising:
the device of claim 1; and
at least one moist treatment surface wherein the moist treatment surface is not a conductive adhesive and wherein the characteristics of the moist treatment surface are controlled in order to attain favorable wound care capabilities.

26. The kit of claim 25, further comprising an active substance, wherein said active substance is effective in wound healing.

27. The kit of claim 25, wherein the at least one moist treatment surface is applied before wound treatment to at least one of the group selected from either the at least one active electrode or the at least one counter electrode, both the at least one active electrode and the at least one counter electrode, the at least one power source, an area above the at least one power source, directly onto the wound and surrounding area, an interface area between two electrodes and a combination thereof.

28. A method of wound treatment, comprising contacting a body area with a wound with the device of claim 1 and with the at least one moist treatment surface.

29. A device for treatment of a wound comprising at least one electrically powered patch comprising:
at least one active electrode;
at least one counter electrode;
at least one power source electrically coupled to the at least one active electrode and at least one counter electrode; and
at least one moist treatment surface disposed on at least one of the at least one active electrode, the at least one counter electrode and the power source,
wherein the moist treatment surface is not a conductive adhesive and wherein the characteristics of the moist treatment surface are controlled in order to attain favorable wound care capabilities, and,
wherein the at least one power source is an open liquid state electrochemical cell comprising: a first layer of insoluble negative pole; a second layer of insoluble positive pole; and a third layer of aqueous electrolyte being disposed between the first and second layers, the third layer comprising at least one of: a deliquescent material for keeping the open cell wet at all times; an electroactive soluble material for obtaining a predetermined ionic conductivity; and a polymer for obtaining a required viscosity for adhering the first and second layers to the third layer.

30. The device of claim 29, wherein the at least one active electrode comprises a metal which is effective in the treatment of wounds.

31. The device of claim 30, wherein the metal is selected from the group consisting of silver and zinc, and wherein generated ions from the metal electrode are effective in wound treatment.

32. The device of claim 29, wherein the device is thin and flexible.

33. The device of claim 29, wherein the characteristics of the at least one moist treatment surface are selected from the group consisting of water content, gelling agents, electrolyte content and pH.

34. The device of claim 29, wherein the at least one moist treatment surface is selected from the group consisting of hydrogel, gel, absorbing substrate and a conductive carrier.

* * * * *